Figure 1:
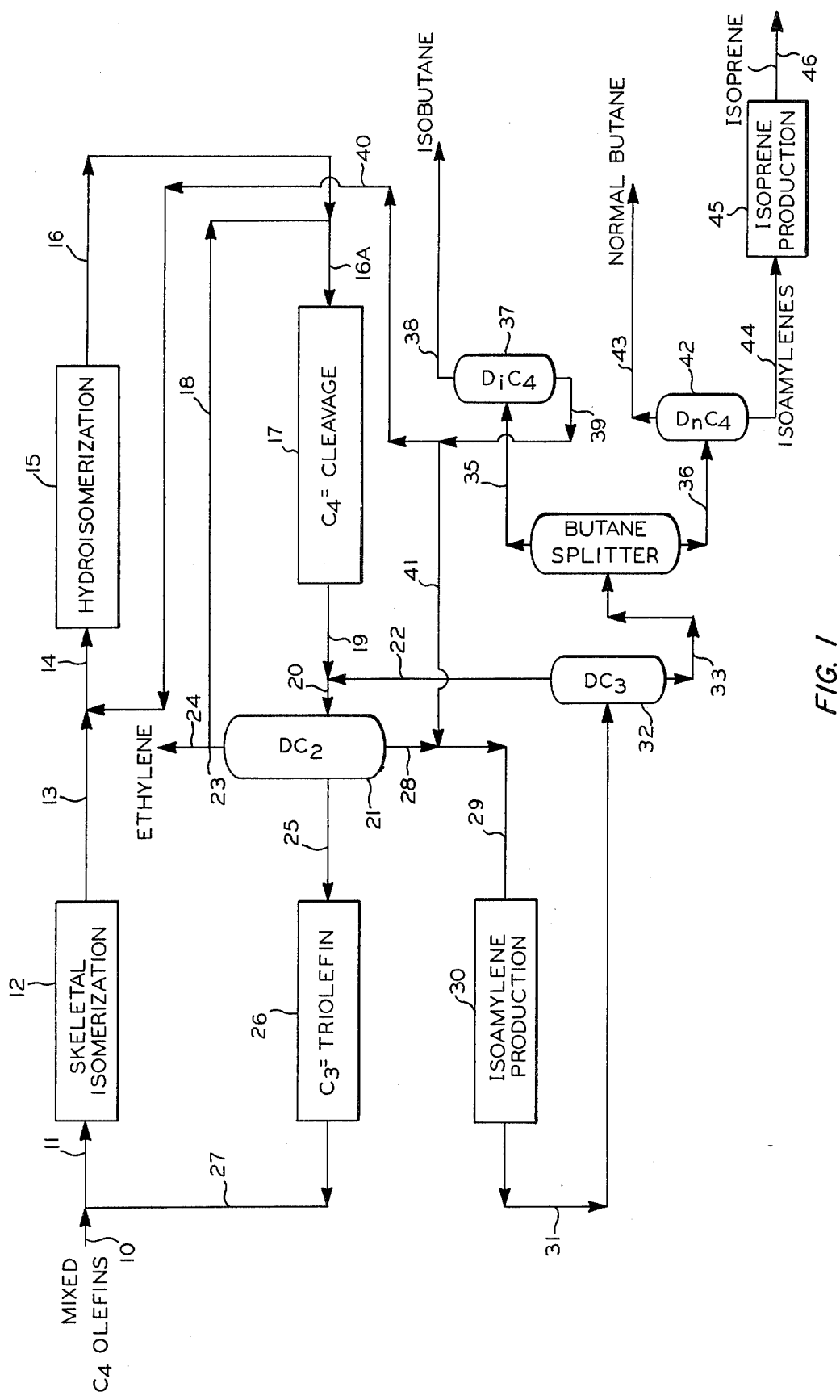

United States Patent [19]

Dixon

[11] 4,176,141
[45] Nov. 27, 1979

[54] ISOAMYLENES FROM BUTENES

[75] Inventor: Rolland E. Dixon, Bartlesville, Okla.

[73] Assignee: Phillips Petroleum Company, Bartlesville, Okla.

[21] Appl. No.: 952,355

[22] Filed: Oct. 18, 1978

[51] Int. Cl.$^2$ .................... C07C 11/10; C07C 3/62; C07C 5/22

[52] U.S. Cl. .................... 585/314; 585/315; 585/316; 585/324; 585/644; 585/670; 585/671

[58] Field of Search .................... 260/683 D, 683.2

[56] References Cited

U.S. PATENT DOCUMENTS

| | | | |
|---|---|---|---|
| 3,565,969 | 2/1971 | Hutton et al. | 260/683 D |
| 3,590,096 | 6/1971 | Banks | 260/683 D |
| 3,590,097 | 6/1971 | Banks et al. | 260/683 D |
| 3,590,098 | 6/1971 | Banks | 260/683 D |
| 3,590,099 | 6/1971 | Banks | 260/683 D |
| 3,621,073 | 11/1971 | McGrath et al. | 260/683 D |
| 3,723,562 | 3/1973 | Heckelsberg | 260/683 D |
| 4,085,158 | 4/1978 | Dixon et al. | 260/683 D |

Primary Examiner—George J. Crasanakis

[57] ABSTRACT

A feed of mixed butenes is subjected to a combination process comprising skeletal isomerization, disproportionation, and appropriate fractionation to yield separate streams of isobutane, normal butane, and isoamylenes which can be dehydrogenated to isoprene.

6 Claims, 1 Drawing Figure

ISOAMYLENES FROM BUTENES

This invention relates to hydrocarbon conversion. In another aspect, this invention relates to the production of isoamylenes from mixed $C_4$ olefins. In another aspect, this invention relates to a method for producing isoprene from a mixed butenes stream. In accordance with a further aspect, this invention relates to a combination process for converting mixed butenes to isoamylenes comprising a combination of steps including skeletal isomerization, hydroisomerization, disproportionation, and fractionation, and optionally, dehydrogenation of yielded isoamylenes to introduce isoprene.

Isoprene is an expensive monomer to manufacture, but highly desirable as a synthetic rubber feedstock. Not only are the polyisoprenes satisfactory for much the same uses as natural rubber, but the polyisoprenes, being pure in composition, for many purposes actually are superior.

Isoprene presently is manufactured, or recovered from various refinery streams such as naphtha cracker by-product streams, only in relatively limited quantities. Small amounts of isoprene are produced in ethylene plants or can be recovered from by-product cracked gasoline produced by some ethylene plants. Some isoamylenes, precursors of isoprene, can be recovered from some cat cracker effluents and dehydrogenated to isoprene. Efforts have been made to produce isoprene by a by-product route involving propylene dimerization, but this has proven uneconomical.

Another source of feedstock that potentially could be useful in making isoamylenes by the triolefin disproportionation reaction has been the availability of various mixed butenes streams from such as a naphtha cracker $C_4$ stream of butylenes or catalytic cracker effluent cut of butylenes. The stumbling block in any such approach has been the need to provide a balanced feed to the triolefin reaction of butenes-2 and isobutene without butene-1. Heretofore, efforts have been made in treating such mixed butenes streams to separate and purify each component, and then recombine butenes-2 and isobutene streams in a suitable proportion for disproportionation. These efforts have been costly and prevented development of a suitable technology.

Accordingly, an object of this invention is to provide an improved process for the production of isoamylenes. A further object of this invention is to provide an improved process for the conversion of mixed olefins to a more valuable product. A further object of this invention is to provide a combination process for yielding separate streams of valuable products.

Other objects, aspects, and the several advantages of the invention will be apparent to those skilled in the art upon reading the specification, the drawing, and the appended claims.

In accordance with the invention, there is now provided a process for producing isoamylenes from mixed $C_4$ olefins comprising the steps of subjecting the mixed $C_4$ olefins to skeletal isomerization, hydroisomerization, disproportionation, and fractionation to yield isoamylenes.

More specifically, in accordance with the invention, a combination process is provided for the production of isoprene from mixed butylenes-butanes comprising the steps of (a) skeletal isomerization of normal butylenes to isobutylene, (b) hydroisomerization of remaining 1-butylene to 2-butylenes, (c) conversion of 2-butylenes to propylene in the presence of added ethylene, (d) conversion of propylene from (c) to 2-butylenes for recycle to skeletal isomerization (a), (e) charging isobutylene and propylene from (c) to produce isoamylenes, and (f) fractionating effluent from (d) to yield isobutane, normal butane containing normal amylenes and isoamylenes which can be dehydrogenated to isoprene.

The skeletal isomerization, the hydroisomerization, and the disproportionation reactions are known in the art. In accordance with this invention, these known processes have been matched in a manner to produce isoamylenes from mixed $C_4$ olefins. The effluents from the various reactions in this invention have to be separated in separation zones. All of these separation zones comprise generally several individual separating units such as fractionation towers, absorber strippers, etc. These units will be explained in some detail in connection with the drawing. It has to be emphasized, however, that the separation actually achieved can be achieved in various manners, and the invention should not be unduly limited to the specific manners in which these separations are shown in the drawing.

BUTENE-1 SKELETAL ISOMERIZATION

When it is desired to convert all or a portion of the butene-1 by skeletal isomerization to isobutene, any means known to the skeletal isomerization arts can be employed. One convenient means for converting butene-1 to isobutene employs an activated catalyst of zirconium oxide, or compound convertible to zirconium oxide upon calcination, preferably promoted by a halogen compound. A presently preferred example can be represented by $ZrOX_2$ wherein X is fluoride, bromide, chloride, or iodide, on alumina. Of these, presently the zirconyl chloride is more preferred. Of the aluminas, pesently preferred are eta- and gamma-alumina, and presently most preferred is eta-alumina. A suitable and exemplary catalyst can be prepared by incorporating about 0.4 to 15 weight percent, preferably about 1 to 10 weight percent, based on the total composition, of zirconyl halide into the selected alumina, such as by impregnating a dried and calcined alumina with an aqueous solution of the desired zirconyl halide, followed by calcination at suitable temperatures such as about 500° F. to 1200° F. for a time such as about 0.1 to 25 hours, in air, or other gas such as nitrogen.

The skeletal isomerization step can be carried out by contacting the feed with the catalyst, using any suitable contacting techniques, at a suitable temperature at which skeletal isomerization of the feed olefin will occur. The temperature preferably is in the range of about 400° to 1200° F. or more, preferably about 600° to 1100° F. The liquid hourly space rate generally will be in the range of about 0.1 to 50, preferably about 0.5 to 30. Any convenient pressure can be used, with the lowest practical pressure preferred in order to minimize side reactions such as polymerization. Pressures ranging from atmospheric to such as about 200 psig are particularly suitable.

BUTENE-1 DOUBLE BOND ISOMERIZATION

One convenient method of converting butene-1 by double bond isomerization or hydroisomerization to butene-2 is by contacting the butene-1 with a catalyst comprising ruthenium oxide. Preferably, the ruthenium oxide is associated with a suitable support material.

Preferred supports include silica, silica-alumina, alumina, and titania. Excellent results are obtained when the support is silica. When the catalyst support is silica, any suitable catalyst grade silica can be employed. Some examples are precipitated silica gel, microspheroidal silica, flame hydrolyzed silica, and silica aerogels. These materials have appreciable surface area, usually in the range of about 50 to 700 m$^3$/g, and can range from fine powders to coarse granules. These materials often contain small amounts of other compounds, including, for example, amounts of alumina and sodium in the order of a few tenths of a percent by weight and smaller. Amounts of these and other materials which do not substantially prevent the desired reaction or unduly promote side reactions are acceptable.

A sufficient amount of the ruthenium oxide is used to obtain the desired activity. Because ruthenium oxide usually is more expensive than the support material, unnecessarily large amounts ordinarily are not used. Generally, the catalyst composite contains about 1 to 15, preferably about 2 to 10, weight percent ruthenium oxide calculated as RuO$_2$, and can be prepared by any suitable method of catalyst preparation, preferably by impregnation. Before use, the catalyst composite can be activated or regenerated by contact with flowing air at elevated temperatures at a time sufficient to produce the desired activity. Activation temperatures in the range of about 800° to 1200° F., for times ranging from about 0.1 to 24 hours, are suitable.

Exemplary conversion temperatures lie in the range of about 200° to 700° F., at any suitable pressure, preferably temperatures in the range of about 300° to 600° F. Pressures in the range of about 0 to 2,00 psig, for example, can be used. The space rate for continuous operation usually will be in the range of about 5 to 15 parts by weight of feed per part by weight of catalyst per hour. After reaction, the reaction mixture can be separated as desired, and unconverted materials recycled to the reaction zone.

The process can be carried out by any suitable contacting technique, either batchwise or continuously, using such as a fixed catalyst bed, stirrer equipped reactor, or other mobile catalyst contacting process.

DISPROPORTIONATION

Triolefin Reaction

In the disproportionation steps of the instant process, the basic reaction is to convert an olefin in the feed to higher and lower molecular weight olefins. The disproportionation reaction is sometimes also generically referred to as the Triolefin process although there are generally more than three olefins involved in the process. In one embodiment of the invention, an effluent from the hydroisomerization unit is passed to a disproportionation zone also referred to herein as a butenes-2 cleavage zone wherein butenes-2 are converted to propylene in the presence of ethylene. In another embodiment, a propylene-rich stream separated from the effluent of the butenes-2 cleavage zone is subjected to disproportionation to produce ethylene and butenes-2. In still another embodiment, a stream comprising isobutane, isobutylene, and some normal butene is charged to a disproportionation zone wherein isobutylene and propylene react to produce isoamylenes and ethylene.

The disproportionation sometimes is termed the "olefin reaction" which can be visualized as comprising the reaction between two first pairs of carbon atoms, the two carbon atoms of each first pair being connected by olefinic double bond, to form two new pairs from the carbon atoms of said first pairs, the two carbon atoms of each of said two new pairs being connected by an olefinic double bond.

Among the suitable catalysts are silica or thoria promoted by an oxide, or a compound convertible to the oxide by calcination, of tungsten, molybdenum, rhenium, or tellurium, or by a sulfide of tungsten or of molybdenum.

Other suitable catalysts include aluminum phosphate, zirconium phosphate, calcium phosphate, magnesium phosphate, or titanium phosphate, promoted by one or more of a sulfide of molybdenum or tungsten, or by an oxide or of a compound convertible to the oxide on calcination, of molybdenum, tungsten, or rhenium, or by magnesium tungstate or beryllium phosphotungstate. These catalysts can be in the form of a powder or granules, as well as a variety of other shapes as is known in the art.

With a fixed bed reactor means in a continuous operation mode, temperatures presently preferred are in the range of about 650° to 850° F., employing a pressure in the range of about 100 to 350 psig, employing a weight hourly space velocity in the range of about 50 to 200, preferably about 75 to 100, weight/weight/hour.

Any mol ratio of reactants can be used. Ideally: in zone 30, one mol of propylene and one mol of isobutylene are used to yield one mol of ethylene and one mol of isoamylenes; in zone 26, two mols of propylene yield one mol of ethylene and one mol of butene-2; and in zone 17, one mol of ethylene and one mol of butenes-2 yield two mols of propylene.

Further details and preferred embodiments of this invention will become apparent to those skilled in the art from the following description of the drawing.

Referring now to the drawing, a feedstream 10 of mixed four carbon hydrocarbons comprising isobutane, normal butane, butene-1, isobutylene, and butenes-2 is charged by line 11 to skeletal isomerization zone 12 wherein normal butenes are isomerized to isobutylene. The reaction product is removed from zone 12 by line 13 and is charged by line 14 to hydroisomerization zone 15 or double bond isomerization zone wherein the butene-1 in the total feed in line 14 is converted to butenes-2 by double bond isomerization.

The effluent from zone 15 comprising ethylene, isobutane, normal butane, butenes-2, isobutylene, some butene-1, and amylenes is charged by line 16 to butenes-2 cleavage zone 17 (disproportionation zone) wherein butenes-2 are converted to propylene in the presence of ethylene. Also introduced into zone 17 is stream 18 which is rich in ethylene and is recovered from subsequent fractionation.

The effluent from zone 17 is passed by lines 19 and 20 to separation zone 21 which is a deethanizer and deethylenizer. Also introduced into separation zone 21 is an ethylene-rich stream 22 separated from subsequent fractionation. An overhead stream 23 rich in ethylene is provided wherein part is passed by line 24 for further processing as desired, e.g., dimerization to butylenes, and the remainder passed by way of line 18 as recycle to the inlet of zone 17. A side cut rich in propylene is removed by line 25 and charged to triolefin zone 26 to produce therefrom ethylene and butenes-2.

The effluent from zone 26 comprising ethylene and butenes-2 is passed by line 27 and introduced as part of the feed to skeletal isomerization zone 12. A bottoms stream 28 comprising isobutylene, isobutane, normal butane, propylene, some butylenes, mainly butene-1, and some amylenes is removed from separation zone 21 and passed by line 29 as feed to Triolefin reaction zone 30.

Typical operating conditions for deethanizer 21 include a suggested top temperature of such as about −20° F., a bottom temperature of such as about 200° F., and an operating pressure of such as about 250 psig.

Disproportionation zone 30 is operated under conditions in the presence of a catalyst such that isobutylene and propylene present in the feed react to produce isoamylenes and ethylene. The reaction product comprising isobutane, normal butane, ethylene, propylene, normal amylene, and isoamylenes is passed by way of line 31 to depropanizer 32 wherein the feedstream in line 31 is subjected to fractionation conditions such that a stream rich in ethylene and propylene is taken overhead by line 22 which is passed as part of the feed to deethanizer 21. In the propylene fractionation means 32 the convenient and presently preferred operating mode employs a top temperature of about 120° F., a bottom temperature of about 200° F., and an operating pressure of the order of about 250 psig effective to remove propylene and ethylene overhead and provide a bottoms stream 33 comprising isobutane, normal butane, normal amylene, and isoamylene.

Bottoms stream 33 removed from separation zone 32 is charged to butane splitter 34 operated under conditions such that an isobutane-rich stream is taken overhead by way of line 35 and a butane-amylenes stream is taken as bottoms by way of line 36.

Overhead 35 removed from zone 34 is charged to deisobutanizer zone 37 which is operated under conditions that isobutane is taken overhead by way of line 38 which can be charged to, for example, HF alkylation (such isobutane being presently in short supply), and the bottoms 39 comprising some isobutane, isobutylene, and butene-1 which is passed either by way of line 40 as part of the feed to hydroisomerization zone 15 or by way of line 41 as part of the feed to disproportionation zone 30.

Bottoms 36, removed from splitter 34, are charged to denormalbutanizer zone 42 operated under conditions such that the overhead 43 comprises normal butane (and contains normal amylene boiling at about 86° F.), and bottoms 44, which is the isoamylenes-rich stream. The isoamylenes so produced then can be subjected to dehydrogenation 45 to produce isoprene 46. This can be accomplished conveniently by oxidative dehydrogenation of the isoamylenes to isoprene, the isoprene being purified by fractionation, not shown.

Splitter 34, deisobutanizer 37, and denormalbutanizer 42 are conventional separation units. The splitter fractionation means, a convenient and presently preferred operating mode, employs a top temperature of about 130° F., a bottom temperature of about 175° F., and an operating pressure of the order of about 110 psig. In the deisobutanizer, the typical operating conditions include a top temperature of about 120° F., a bottom temperature of about 150° F., and an operating pressure of about 100 psig. Typical operating conditions for the denormalbutanizer include a top temperature of about 90° F., a bottom temperature of about 150° F., and an operating pressure of about 40 psig.

The operations for catalytic reactions in units 12, 15, 17, 26, and 30 are also well known in the art. The best mode of operation for this invention for pressures and temperatures are given below.

|  | Temperature °F. | Pressure psig |
|---|---|---|
| Unit 12 | 900 | 100 |
| Unit 15 | 300 | 150 |
| Unit 17 | 750 | 100 |
| Unit 26 | 750 | 150 |
| Unit 30 | 750 | 250 |

Low pressure is preferred in unit 12. By adding "ethylene" stream 27 to unit 12, operation is at the higher 100 psig to minimize compression requirements, e.g., for subsequent reaction unit 17. Pressure is not particularly significant within a reasonable range in unit 17. A pressure close to upstream unit is used. Again, pressure is not particularly significant within reason in zone or unit 26. Pressure is chosen for upstream and downstream units. Also, pressure is not particularly significant within reason in zone or unit 30. Pressure is chosen for desired operations of subsequent fractionation. Unit 12 can have a pressure range of about atmospheric to about 125 psig and temperature range of about 700° F. to 950° F. Best operation, with ethylene recycle for lowering partial pressure of butylenes, is about 100 psig and 900° F.

The following calculated example is given to further illustrate the invention and is not intended to limit the scope thereof. This example shows the calculated material balance for the conversion of mixed $C_4$ olefins to isoamylenes. The numerals of the various streams shown in the following table refer to the reference numerals of the corresponding stream in the drawing. The calculated example is based on a feed of 190,000 metric tons per year.

| | THOUSAND METRIC TONS PER YEAR | | | | | | | | | |
|---|---|---|---|---|---|---|---|---|---|---|
| STREAM | Ethylene | Propylene | Isobutane | Isobutylene | Butene-1 | Normal Butane | Butenes-2 | Isopentene | Normal Pentene | Total |
| 10 | — | — | 4 | 16 | 131 | 26 | 13 | — | — | 190 |
| 13 | 84 | 345 | 4 | 102 | 58 | 26 | 143 | — | 14 | 776 |
| 14 | 135 | 345 | 4 | 226 | 85 | 28 | 143 | — | 14 | 980 |
| 16 | 135 | 345 | 4 | 226 | 18 | 28 | 210 | — | 14 | 980 |
| 16A | 1,192 | 345 | 4 | 226 | 18 | 28 | 210 | — | 14 | 2,037 |
| 19 | 1,086 | 668 | 4 | 226 | 27 | 28 | — | — | 3 | 2,041 |
| 20 | 1,086 | 761 | 4 | 226 | 27 | 28 | — | — | 3 | 2,135 |
| 23 | 1,086 | — | — | — | — | — | — | — | — | 1,086 |
| 18 | 1,056 | — | — | — | — | — | — | — | — | 1,056 |
| 24 | 30 | — | — | — | — | — | — | — | — | 30 |
| 28 | — | 170 | 4 | 226 | 27 | 28 | — | — | 3 | 458 |
| 29 | — | 170 | 4 | 226 | 27 | 28 | — | — | 3 | 458 |
| 31 | 51 | 93 | 4 | 124 | 27 | 28 | — | 127 | 3 | 457 |
| 22 | — | 93 | — | — | — | — | — | — | — | 93 |
| 25 | — | 591 | — | — | — | — | — | — | — | 591 |

-continued

THOUSAND METRIC TONS PER YEAR

| STREAM | Ethylene | Propylene | Isobutane | Isobutylene | Butene-1 | Normal Butane | Butenes-2 | Isopentene | Normal Pentene | Total |
|---|---|---|---|---|---|---|---|---|---|---|
| 27 | 83 | 343 | — | — | — | — | 166 | — | — | 592 |
| 43 | — | — | — | — | — | 26 | — | — | 3 | 29 |
| 44 | — | — | — | — | — | — | — | 127 | — | 127 |
| 33 | 51 | — | 4 | 124 | 27 | 28 | — | 127 | 3 | 364 |
| 35 | 51 | — | 4 | 124 | 27 | 1 | — | — | — | 207 |
| 39 | 51 | — | — | 124 | 27 | 1 | — | — | — | 203 |
| 36 | — | — | — | — | — | 26 | — | 127 | 3 | 156 |
| 38 | — | — | 4 | — | — | — | — | — | — | 4 |
| 40 | 51 | — | — | 124 | 27 | 1 | — | — | — | 203 |
| 11 | 82 | 342 | 4 | 16 | 131 | 26 | 178 | — | — | 779 |

METRIC TONS PER YEAR

| Butanes-Butylenes | Feed | Products | | | | | Atmosphere Boiling Point, °F. |
|---|---|---|---|---|---|---|---|
|  |  | Ethylene | Iso-butane | Normal Butane | Normal Pentenes | Iso-pentene |  |
| Ethylene | — | 30,015 | — | — | — | — | −154.7 |
| Isobutane | 3,610 | — | 3,610 | — | — | — | +10.9 |
| Isobutylene | 16,340 | — | — | — | — | — | +19.6 |
| Butene-1 | 131,100 | — | — | — | — | — | +20.7 |
| Normal Butane | 26,200 | — | — | 26,200 | — | — | +31.1 |
| Butenes-2 | 12,730 | — | — | — | — | — | +33.6, 38.7 |
| Isoamylene | — | — | — | — | — | 127,334 | 2,2 (+101.2) |
| Normal Pentenes | — | — | — | — | 2,733 | — | +84.6 (1-pentene) |
| Total | 190,000 | 30,015 | 3,610 | 26,220 | 2,733 | 127,334 |  |
| BP, °F. | (1 atm.) | (−154.7) | (10.9) | (31.1) | (84.6) | (101.2) |  |

I claim:

1. A process for converting mixed butenes to isoamylenes which comprises the steps of
   (a) passing a first stream comprising mixed butenes to a skeletal isomerization zone and therein subjecting same to isomerization conditions sufficient to convert normal butenes to isobutylene,
   (b) passing the reaction product from (a) to a hydroisomerization zone and therein subjecting same to double bond isomerization conditions sufficient to convert butene-1 to butenes-2,
   (c) passing the effluent from (b) comprising ethylene, isobutane, normal butane, butenes-2, isobutylene, butene-1, and amylenes to a butenes-2 cleavage zone or disproportionation zone wherein butenes-2 are converted to propylene in the presence of ethylene,
   (d) separating the effluent from (c) into an overhead ethylene-rich stream, a propylene-rich side stream, and a bottoms stream comprising isobutylene, isobutane, normal butane, propylene, some butylenes, and some amylenes,
   (e) passing said bottoms stream (d) to a disproportionation zone and therein subjecting same to disproportionation conditions such that isobutylene and propylene react to form isoamylenes and ethylene, and
   (f) separating the effluent from (e) into separate streams comprising (1) an ethylene/propylene-rich stream, (2) an isobutane-rich stream, (3) a normal butane-rich stream, (4) an isobutane/isobutylene/isobutene-1 containing stream, and (4) an isoamylenes-rich stream.

2. A process according to claim 1 wherein a portion of said overhead ethylene-rich stream separated in (d) is recycled as a portion of the feed to (c).

3. A process according to claim 1 wherein said propylene-rich side stream separated in (d) is passed to a disproportionation zone and subjected to disproportionation conditions to convert propylene to ethylene and butenes which are charged as part of the feed to skeletal isomerization zone (a).

4. A process according to claim 1 wherein said stream (4) in step (f) comprising isobutane, isobutylene, and butene-1 is split with a portion being passed as part of the feed to hydroisomerization zone (b) and another portion being passed as a portion of the feed to disproportionation zone (e).

5. A process according to claim 1 wherein said ethylene/propylene-rich stream (1) separated in (f) is passed with the effluent from (c) to separation (d).

6. A process according to claim 1 further comprising the steps of
   (g) passing a portion of said overhead ethylene-rich stream separated in (d) as a portion of the feed to (c),
   (h) passing said propylene-rich side stream to disproportionation zone to convert propylene to ethylene and butenes which are charged as part of the feed to skeletal isomerization zone (a),
   (i) passing a portion of said stream (4) in step (f) as part of the feed to (b) and another portion as part of the feed to (e), and
   (j) passing said ethylene/propylene-rich stream (1) in step (f) as a portion of the feed to separation (d).

* * * * *